United States Patent
Stulen et al.

(10) Patent No.: US 7,163,548 B2
(45) Date of Patent: Jan. 16, 2007

(54) ULTRASONIC SURGICAL BLADE AND INSTRUMENT HAVING A GAIN STEP

(75) Inventors: Foster B. Stulen, Mason, OH (US); Steven K. Neuenfeldt, Cincinnati, OH (US); Kevin L. Houser, Springboro, OH (US)

(73) Assignee: Ethicon Endo-Surgery, Inc, Cincinnati, OH (US)

( * ) Notice: Subject to any disclaimer, the term of this patent is extended or adjusted under 35 U.S.C. 154(b) by 158 days.

(21) Appl. No.: 10/701,588

(22) Filed: Nov. 5, 2003

(65) Prior Publication Data

US 2005/0096679 A1    May 5, 2005

(51) Int. Cl.
*A61B 17/32* (2006.01)
*A61C 1/07* (2006.01)
*A61C 3/03* (2006.01)

(52) U.S. Cl. .................. 606/159; 604/22; 601/46; 433/119

(58) Field of Classification Search ............. None
See application file for complete search history.

(56) References Cited

U.S. PATENT DOCUMENTS

| | | | |
|---|---|---|---|
| 5,112,300 A | 5/1992 | Ureche | |
| 5,180,363 A | 1/1993 | Idemoto et al. | |
| 5,269,297 A | 12/1993 | Weng et al. | |
| 5,318,570 A * | 6/1994 | Hood et al. | 606/99 |
| 5,380,274 A | 1/1995 | Nita | |
| 5,527,273 A | 6/1996 | Manna et al. | |
| 5,695,510 A | 12/1997 | Hood | |
| 5,746,756 A | 5/1998 | Bromfield et al. | |
| 5,971,949 A | 10/1999 | Levin et al. | |
| 6,227,853 B1 * | 5/2001 | Hansen et al. | 433/119 |
| 6,254,623 B1 | 7/2001 | Haibel et al. | |
| 6,309,400 B1 | 10/2001 | Beaupre | |
| 6,328,751 B1 | 12/2001 | Beaupre | |
| 6,423,082 B1 | 7/2002 | Houser et al. | |
| 6,432,118 B1 | 8/2002 | Messerly | |
| 6,652,547 B1 | 11/2003 | Rabiner et al. | |
| 6,660,017 B1 | 12/2003 | Beaupre | |
| 6,773,444 B1 * | 8/2004 | Messerly | 606/169 |

OTHER PUBLICATIONS

PCT Search report dated Dec. 2, 2005 for corresponding international patent number PCT/US04/36897.

* cited by examiner

*Primary Examiner*—Glenn K. Dawson

(57) ABSTRACT

An ultrasonic surgical blade, and an instrument, having a gain step. The blade body has, in any half wave length of the ultrasonic-surgical-blade body, a first vibration antinode, a vibration node, a second vibration antinode, and a gain step. The gain step is located between the second vibration antinode and the first vibration antinode. The gain step is spaced apart from the vibration node by a gain-step distance greater than 5% of the distance between the second vibration antinode and the first vibration antinode. The instrument includes the blade, a handpiece having an ultrasonic transducer, and an ultrasonic transmission rod whose proximal end is operatively connected to the ultrasonic transducer and whose distal end activates the blade. In one option, the first vibration antinode is the distal tip, and the gain step is located between the vibration node and the distal tip, resulting in an increased active length of the blade.

12 Claims, 3 Drawing Sheets

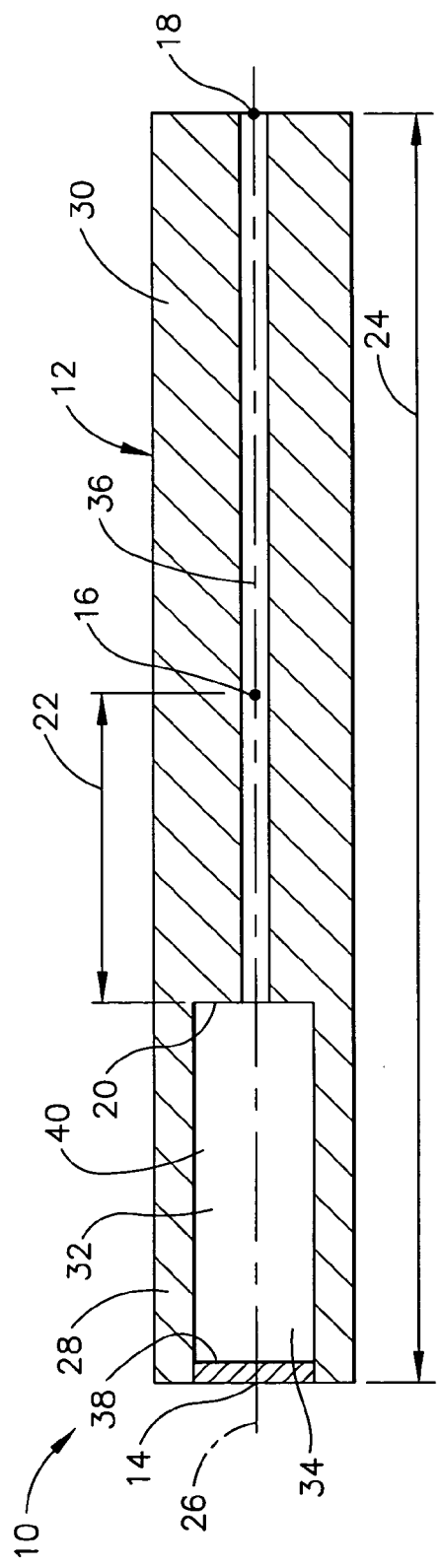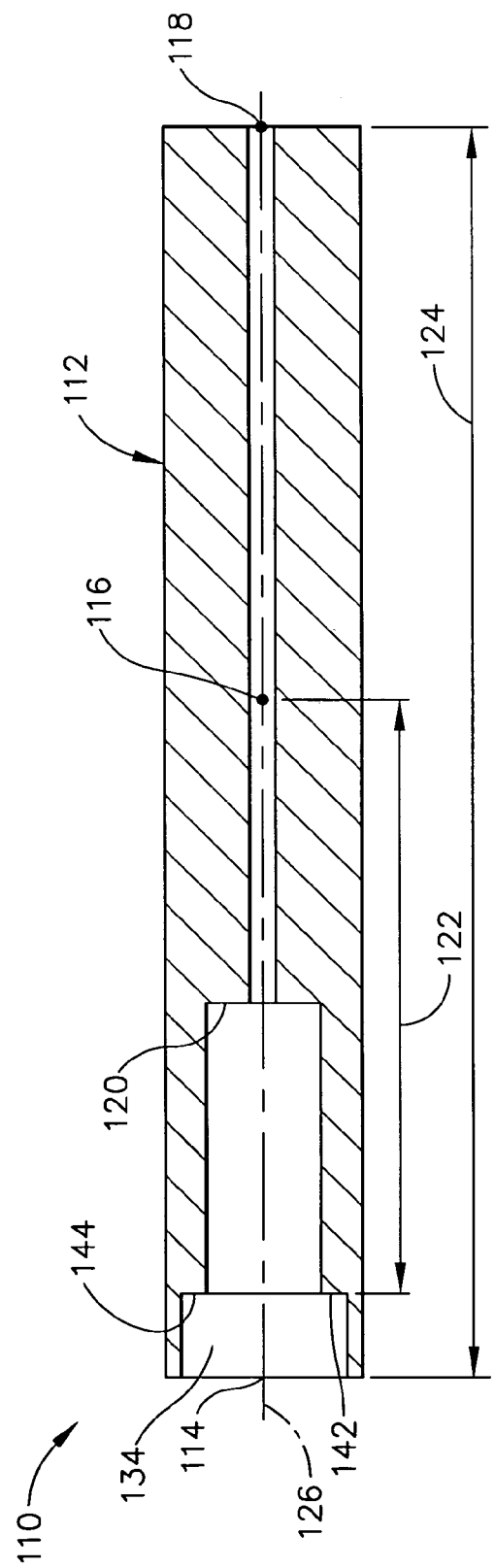

ULTRASONIC SURGICAL BLADE AND INSTRUMENT HAVING A GAIN STEP

FIELD OF THE INVENTION

The present invention relates generally to ultrasonic surgical blades and ultrasonic surgical instruments which include ultrasonic surgical blades, and more particularly to those having a gain step.

BACKGROUND OF THE INVENTION

Ultrasonic surgical instruments are known which include ultrasonic surgical blades. A handpiece of a known ultrasonic surgical instrument includes an ultrasonic transducer which is powered by an ultrasonic generator through a cable. An ultrasonic transmission rod of the instrument has a proximal end and a distal end, wherein the proximal end is operatively connected to the ultrasonic transducer. An ultrasonic surgical blade is activated by the distal end of the ultrasonic transmission rod. Known blade shapes include straight blades and curved blades and include blades that are symmetric and blades that are asymmetric about a longitudinal axis or about a curved centerline of the blade.

A known ultrasonic surgical blade is a cylindrical blade which has a distal tip, a most-distal vibration node (a vibration node being a point of substantially zero displacement), and a second most-distal vibration antinode (a vibration antinode being a point of maximum displacement relative to all other points in a half wave), wherein the most-distal vibration antinode is the distal tip. Longitudinal ultrasonic vibration of the blade generates motion and heat in the contacted tissue, wherein the heat primarily provides the means for the blade to cut and/or coagulate patient tissue. The blade has a gain step located a distance from the most-distal vibration node which is less than 5% of the distance between the distal tip and the second-most-distal vibration antinode because locating the gain step close to the most-distal vibration node maximizes the vibration amplitude gain. The known blade consists of a larger-diameter right-circular geometrically-solid cylinder from the second most-distal vibration antinode to the most-distal vibration node. The known blade consists of a smaller-diameter right-circular geometrically-solid cylinder from the most-distal vibration node to the distal tip. The change in diameter provides a gain in vibration amplitude for the smaller-diameter section of the blade equal to the ratio of the transverse cross-sectional areas of the larger diameter blade section to the smaller diameter blade section when the gain step is located at the node.

The active length of an ultrasonic surgical blade is defined by applicants as the distance from the distal tip to where the vibration amplitude (i.e., the longitudinal vibration amplitude) has fallen to 50% of the tip amplitude. The blade is not considered useful beyond its active length. The active length is about 15 mm for a straight cylindrical titanium rod at a resonant frequency of about 55.5 kHz.

It is known in ultrasonic welding of plastics to provide an ultrasonic welding rod having a gain step, such as a discontinuity between a larger and a smaller rod diameter, which is located between the most-distal vibration node and the distal end of the welding horn and which is spaced apart from the most-distal vibration node of the welding rod by a distance less than 5% of the distance between the second-most-distal vibration antinode and the distal end of the welding rod. It is also known in ultrasonic welding of plastics to provide an ultrasonic welding rod with a hole or a slot to provide a gain in longitudinal vibration amplitude.

What is needed is an improved ultrasonic surgical blade, and an improved ultrasonic surgical instrument which includes an ultrasonic surgical blade, having a longer or shorter active length.

SUMMARY OF THE INVENTION

A first expression of an embodiment of the invention is for an ultrasonic surgical blade including an ultrasonic-surgical-blade body. The ultrasonic-surgical-blade body has a distal tip which is a most-distal vibration antinode, has a most-distal vibration node, has a second-most-distal vibration antinode, and has a gain step. The gain step is located between the second-most-distal vibration antinode and the distal tip, and the gain step is spaced apart from the most-distal vibration node by a gain-step distance greater than 5% of the distance between the second-most-distal vibration antinode and the distal tip.

A second expression of an embodiment of the invention is for an ultrasonic surgical instrument including a handpiece, an ultrasonic transmission rod, and an ultrasonic surgical blade. The handpiece includes an ultrasonic transducer. The ultrasonic transmission rod has a proximal end and a distal end, wherein the proximal end is operatively connected to the ultrasonic transducer. The ultrasonic surgical blade is activated by the distal end and includes an ultrasonic-surgical-blade body. The ultrasonic-surgical-blade body has a distal tip which is a most-distal vibration antinode, has a most-distal vibration node, has a second-most-distal vibration antinode, and has a gain step. The gain step is located between the second-most-distal vibration antinode and the distal tip, and the gain step is spaced apart from the most-distal vibration node by a gain-step distance greater than 5% of the distance between the second-most-distal vibration antinode and the distal tip.

A third expression of an embodiment of the invention is for an ultrasonic surgical blade including an ultrasonic-surgical-blade body. The ultrasonic-surgical-blade body has, in any half wave length of the ultrasonic-surgical-blade body, a first vibration antinode, a vibration node, a second vibration antinode, and a gain step. The gain step is located between the second vibration antinode and the first vibration antinode. The gain step is spaced apart from the vibration node by a gain-step distance greater than 5% of the distance between the second vibration antinode and the first vibration antinode.

Several benefits and advantages are obtained from one or more of the expressions of the embodiment of the invention. Applicants found that locating a gain step having a gain greater than unity (i.e., an amplification step) further than conventionally taught from the most-distal vibration node toward the distal tip further increased the active length of the ultrasonic surgical blade even though the vibration amplitude gain was less than when conventionally locating the gain step closer to the most-distal vibration node. Applicants determined that locating the gain step further than conventionally taught from the most-distal vibration node toward the second-most-distal vibration antinode should shorten the half wave length of the ultrasonic surgical blade. Applicants also determined that such changes in active and half wave lengths of the ultrasonic surgical blade would also result from gain steps having gains less than unity (i.e., a deamplification step) but with a deamplification step causing a decrease in active length where an identically located amplification step would cause an increase in active length and with a deamplification step causing an increase in active length where an identically located amplification step would cause a decrease in active length. Being able to lengthen or shorten the active length of an ultrasonic surgical blade offers advantages for particular surgical applications, as can be appreciated by those skilled in the art.

The present invention has, without limitation, application in robotic-assisted surgery.

BRIEF DESCRIPTION OF THE DRAWINGS

FIG. 2 is a longitudinal cross-sectional view of the most-distal one-half wavelength, including the distal tip, of the ultrasonic surgical blade of FIG. 1;

FIG. 3 is a longitudinal cross-sectional view of the most-distal one-half wavelength, including the distal tip, of a second embodiment of the surgical blade of FIG. 1.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is understood that any one or more of the following-described expressions of an embodiment, examples, etc. can be combined with any one or more of the other following-described expressions of an embodiment, examples, etc. For example, and without limitation, a gain feature of a reduced diameter can be combined with a gain feature of a hole.

Figure 1:
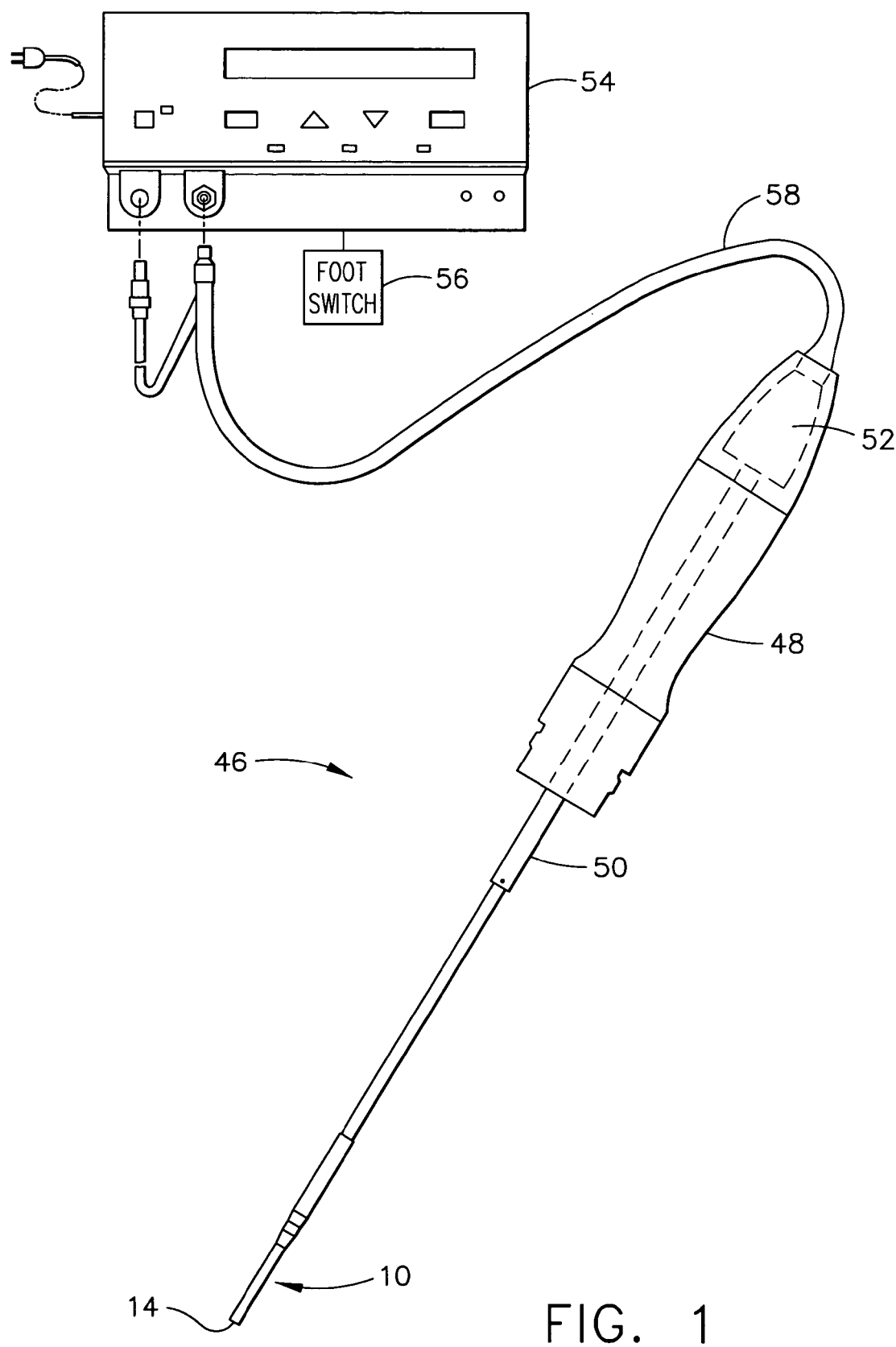
FIG. 1 is a schematic view of a first embodiment of an ultrasonic surgical instrument including a first embodiment of an ultrasonic surgical blade of the invention.

Referring now to the drawings, FIGS. 1–2 illustrate a first embodiment of the invention. A first expression of the first embodiment of FIGS. 1–2 is for an ultrasonic surgical blade 10 including an ultrasonic-surgical-blade body 12 having a distal tip 14 which is a most-distal vibration antinode (a vibration antinode being a point of maximum displacement relative to all other points in a half wave), having a most-distal vibration node 16 (a vibration node being a point of substantially zero displacement), having a second-most-distal vibration antinode 18, and having a gain step 20. The gain step 20 is disposed between the second-most-distal vibration antinode 18 and the distal tip 14 and is spaced apart from the most-distal vibration node 16 by a gain-step distance 22 greater than 5% of the distance 24 between the second-most-distal vibration antinode 18 and the distal tip 14.

In one implementation of the first expression of the first embodiment of FIGS. 1–2, the gain step distance 22 is between substantially 25% and substantially 45% of the distance 24 between the second-most-distal vibration antinode 18 and the distal tip 14. Those of ordinary skill in the art, employing the teachings of the invention for the location of the gain step 20, can create analytical blade models and evaluate them using a computer program to optimize design trade-offs between increased or decreased active length of the ultrasonic surgical blade and increased or decreased amplitude of the longitudinal ultrasonic vibrations for locating the gain step 20 substantially away from the most-distal vibration node 16 in the direction of the distal tip 14 or in the direction of the second-most-distal vibration antinode 18.

In one example of the first expression of the first embodiment of FIGS. 1–2, between the second-most-distal vibration antinode 18 and the distal tip 14, the maximum vibration amplitude of the ultrasonic-surgical-blade body 12 proximal the gain step 20 is less than the maximum vibration amplitude of the ultrasonic-surgical-blade body 12 distal the gain step 20. In this example, the gain of the gain step 20 is greater than unity and results from a reduction in mass of the ultrasonic-surgical-blade body 12 between the gain step 20 and the distal tip 14 compared to the mass of the ultrasonic-surgical-blade body 12 between the gain step 20 and the second-most-distal vibration antinode 18.

In a different embodiment, not shown, between the second-most-distal vibration antinode and the distal tip, the maximum vibration amplitude of the ultrasonic-surgical-blade body proximal the gain step is greater than the maximum vibration amplitude of the ultrasonic-surgical-blade body distal the gain step. In this embodiment, the gain of the gain step is less than unity and results from an increase in mass of the ultrasonic-surgical-blade body between the gain step and the distal tip compared to the mass of the ultrasonic-surgical-blade body between the gain step and the second-most-distal vibration antinode. This embodiment can be easily visualized, in one example, by switching the locations of the distal tip 14 and the second-most-distal vibration antinode 18 in FIG. 2.

In one enablement of the first expression of the first embodiment of FIGS. 1–2, the gain step 20 is disposed between the most-distal vibration node 16 and the distal tip 14 resulting in an increased active length of the ultrasonic surgical blade 10. In a different embodiment, not shown, the gain step is disposed between the most-distal vibration node and the second-most-distal vibration antinode resulting in a decreased half wave length of the ultrasonic surgical blade. This embodiment can be easily visualized by moving the gain step 20 between the most-distal vibration node 16 and the second-most-distal vibration antinode 18 in FIG. 2.

In one illustration of the first expression of the first embodiment of FIGS. 1–2, the ultrasonic-surgical-blade body 12 has a longitudinal axis 26 and consists essentially of a first geometric solid 28 having a substantially constant first transverse cross-sectional area from the gain step 20 to the distal tip 14 and a second geometric solid 30 having a substantially constant second transverse cross-sectional area from the gain step 20 to the second-most-distal vibration antinode 18. The second transverse cross-sectional area is different than the first transverse cross-sectional area. In one variation, the shape and size of the first external perimeter of the first transverse cross-sectional area is substantially equal to the shape and size of the second external perimeter of the second transverse cross-sectional area. In one modification, at least one of the first and second transverse cross-sectional areas surrounds a void 32. In one construction, the void 32 includes a first longitudinal hole 34 which is disposed in the first geometric solid 28 and which extends proximally from the distal tip 14. Applicants found that locating the gain step 20 at the point where the gain equaled the square root of the ratio of the transverse cross-sectional areas of the second geometric solid 30 to the first geometric solid 28 optimized the increase in the active length of the blade. In one arrangement, the void 32 includes a second longitudinal hole 36 which is disposed in the second geometric solid 30 and which is in fluid communication with the first longitudinal hole 34, and the first and second longitudinal holes 34 and 36 are adapted for irrigation and/or suction. In another arrangement, the ultrasonic surgical blade 10 also includes a membrane 38 which has a composition substantially the same as the composition of the ultrasonic-surgical-blade body 12, which covers the first longitudinal hole 34, and which is removably or permanently attached to the first geometric solid 28 at the distal tip 14. It is noted that the membrane 38 would be removed from the first geometric solid 28 in FIG. 2 when irrigation and/or suction is desired. Alternatively, membrane 38 may be made from a permeable fabric, such as a wire mesh or screen, or sintered mesh made from titanium or other appropriate material to facilitate irrigation and/or suction.

In a different embodiment, not shown, the ultrasonic-surgical-blade body has a longitudinal axis and consists essentially of a first geometric solid and a second geometric solid. The first geometric solid has a first mass, extends from the gain step to the distal tip, and has a non-constant first transverse cross-sectional area. The second geometric solid has a second mass, extends from the gain step to the second-most-distal vibration antinode, and has a non-constant second transverse cross-sectional area. The second mass is different than the first mass. This embodiment is easily visualized, in one example, by considering the second longitudinal hole 36 to have a diameter which decreases from the second-most-distal vibration antinode 18 to the gain step 20 and the first longitudinal hole 34 to have a diameter which increases from the gain step 20 to the distal tip 14 in FIG. 2. The variations, modifications, etc. of the preceding paragraph are equally applicable to this embodiment.

In a further embodiment, not shown, the ultrasonic surgical blade body has a longitudinal axis and consists essentially of a first geometric solid having a first mass and having a first axial length extending from the gain step to the distal tip and a second geometric solid having a second mass and having a second axial length extending from the gain step to the second-most-distal vibration antinode. The second mass is different than the first mass. One of the first and second geometric solids has a substantially constant transverse cross-sectional area along its corresponding axial length, and a different one of the first and second geometric solids has a non-constant transverse cross-sectional area along its corresponding axial length. This embodiment is easily visualized, in one example, by considering the first longitudinal hole 34 to have a diameter which increases from the gain step 20 to the distal tip 14 in FIG. 2. The variations, modifications, etc. of the second preceding paragraph are equally applicable to this embodiment.

In one design of the first expression of the first embodiment of FIGS. 1–2, the ultrasonic-surgical-blade body 12 has a longitudinal axis 26 and is substantially symmetrical about the longitudinal axis 26. In another design, not shown, the ultrasonic-surgical-blade body has a longitudinal axis, has an active length, and is substantially asymmetric about the longitudinal axis along at least a portion of the active length. In one variation, the ultrasonic-surgical-blade body is curved. This variation is easily visualized, in one example, by curving the distal portion of the ultrasonic-surgical-blade body 12 upward from the longitudinal axis 26 in FIG. 2.

In one deployment of the first expression of the first embodiment of FIGS. 1–2, the ultrasonic-surgical-blade body 12 has at least one gain feature 40 selected from the group consisting of: a discrete change in outer diameter or perimeter, a taper, a longitudinal hole, a discrete change in diameter of a longitudinal hole, a transverse hole, a surface flat, and a surface slot. It is noted that, in this deployment, the gain step 20 is the location of the portion of the gain feature 40 which is closest to the most-distal vibration node 16. It is also noted that the term "hole" includes a through hole and a non-through hole. Other gain features are left to the artisan.

FIG. 3 illustrates a second embodiment of the ultrasonic surgical blade 110 of the invention. In this embodiment, the ultrasonic-surgical-blade body 112 has an additional gain step 142 which is spaced-apart from the gain step 120, which is disposed between the second-most-distal vibration antinode 118 and the distal tip 114, and which is spaced apart from the most-distal vibration node 116 by a gain-step distance 122 greater than 5% of the distance 124 between the second-most-distal vibration antinode 118 and the distal tip 114. The ultrasonic-surgical-blade body 112 has a longitudinal axis 126 and a longitudinally hole 134, wherein the longitudinal hole has a shoulder 144 defining the additional gain step 142.

Figure 4:
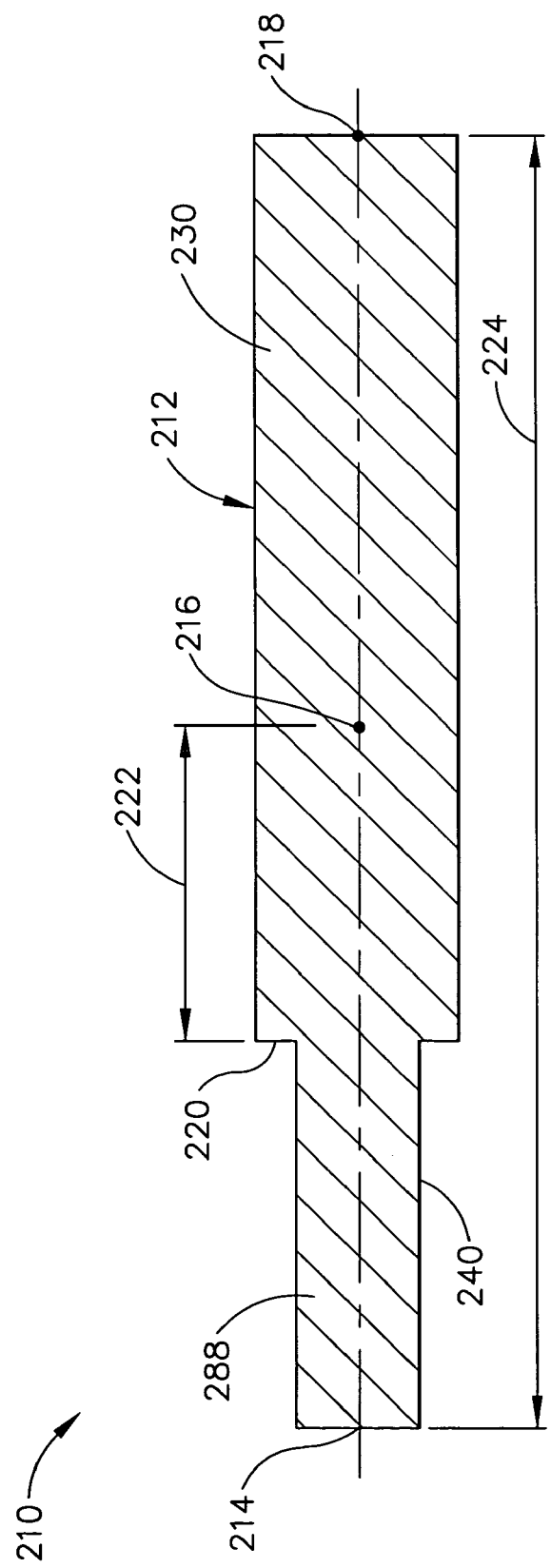
FIG. 4 is a longitudinal cross-sectional view of the most-distal one-half wavelength, including the distal tip, of a third embodiment of the surgical blade of FIG. 1.

A third embodiment of an ultrasonic surgical blade 210 is shown in FIG. 4, wherein the ultrasonic-surgical-blade body 212 consists essentially of a right-circular first geometrically-solid cylinder 288 from the gain step 220 to the distal tip 214. In this embodiment, the ultrasonic-surgical-blade body 212 consists essentially of a right-circular second geometrically-solid cylinder 230 from the gain step 220 to the second-most-distal vibration antinode 218. The diameter of the first geometrically-solid cylinder 288 is less than the diameter of the second geometrically-solid cylinder 230. It is noted that in this embodiment, the gain feature 240 is a reduced diameter from the distal tip 214 to the gain step 220 which reduces mass and which creates the first geometrically-solid cylinder 288. The gain step 220 is disposed between the second-most-distal vibration antinode 218 and the distal tip 214 and is spaced apart from the most-distal vibration node 216 by a gain-step distance 222 greater than 5% of the distance 224 between the second-most-distal vibration antinode 218 and the distal tip 214.

In one construction of the first expression of the first embodiment of FIGS. 1–2, the ultrasonic-surgical-blade body 12 consists essentially of titanium. In other constructions, blade bodies consist essentially of aluminum, a ceramic, sapphire, or any other material that transmits ultrasound in an efficient manner. Mathematical analysis of various titanium blade designs using the described principles of the invention calling for locating the gain step 20 substantially away from the most-distal vibration node 16 in the direction of the distal tip 14 achieved increases in the active length of the ultrasonic surgical blade 10 up to 40%. Applicants have seen increases up to 60% in theory. As previously mentioned, the active length of an ultrasonic surgical blade 10 is defined as the distance from the distal tip 14 to where the vibration amplitude (i.e., the longitudinal vibration amplitude) has fallen to 50% of the tip amplitude. The blade is not considered useful beyond its active length. The active length is about 15 mm for a straight cylindrical titanium rod at a resonant frequency of about 55.5 kHz without applying the principles of the invention. An increase in active length up to about 5 mm can be expected using the described principles of the invention when the gain step 20 is disposed between the most-distal vibration node 16 and the distal tip 14.

In one arrangement, the ultrasonic surgical blade 10 is used alone as the end effector of an ultrasonic surgical instrument. In another arrangement, the ultrasonic surgical blade 10 is used with a clamp arm (not shown) to create a shears end effector of an ultrasonic surgical instrument for cutting and/or coagulating patient tissue.

A second expression of the first embodiment of FIGS. 1–2 is for an ultrasonic surgical instrument 46 including a handpiece 48, an ultrasonic transmission rod 50, and an ultrasonic surgical blade 10. The handpiece 48 includes an ultrasonic transducer 52. The ultrasonic transmission rod 50 has a proximal end and a distal end, wherein the proximal end is operatively connected to the ultrasonic transducer 52. The ultrasonic surgical blade 10 is activated by the distal end and includes an ultrasonic-surgical-blade body 12. The ultrasonic-surgical-blade body 12 has a distal tip 14 which is a most-distal vibration antinode, has a most-distal vibration node 16, has a second-most-distal vibration antinode 18, and has a gain step 20. The gain step 20 is disposed between the second-most-distal vibration antinode 18 and the distal tip 14 and is spaced apart from the most-distal vibration node 16 by a gain-step distance 22 greater than 5% of the distance 24 between the second-most-distal vibration antinode 18 and the distal tip 14.

In one enablement of the second expression of the first embodiment of FIGS. 1–2, there is also included an ultrasonic generator 54, activated by a foot pedal 56, and a cable 58 operatively connecting the ultrasonic generator 54 and the ultrasonic transducer 52 of the handpiece 48. In one construction, the ultrasonic surgical blade 10 is a monolithic portion of the ultrasonic transmission rod 50. In another construction, the ultrasonic surgical blade is a separate piece and is attached to the ultrasonic transmission rod. It is noted that the embodiments, implementations, examples, illustrations, etc. previously described for the ultrasonic surgical blade are equally applicable to the ultrasonic surgical instrument.

A third expression of the first embodiment of FIGS. 1–2 is for an ultrasonic surgical blade including an ultrasonic-surgical-blade body having, in any half wave length of the ultrasonic-surgical-blade body, a first vibration antinode, a vibration node, a second vibration antinode, and a gain step, wherein the gain step is disposed between the second vibration antinode and the first vibration antinode, and wherein the gain step is spaced apart from the vibration node by a gain-step distance greater than 5% of the distance between the second vibration antinode and the first vibration antinode. It is noted that the third expression does not limit the location of the half wave to the last half wave length of the blade body as with the previously presented second expression, and that apart from the second expression's location of the half wave, the embodiments, implementations, examples, illustrations, etc. previously described for the second expression are equally applicable to the third expression.

Several benefits and advantages are obtained from one or more of the expressions of the embodiment of the invention. Applicants found that locating a gain step having a gain greater than unity (i.e., an amplification step) further than conventionally taught from the most-distal vibration node toward the distal tip further increased the active length of the ultrasonic surgical blade even though the vibration amplitude gain was less than when conventionally locating the gain step closer to the most-distal vibration node. Applicants determined that locating the gain step further than conventionally taught from the most-distal vibration node toward the second-most-distal vibration antinode should shorten the half wave length of the ultrasonic surgical blade. Applicants also determined that such changes in active and half wave lengths of the ultrasonic surgical blade would also result from gain steps having gains less than unity (i.e., a deamplification step) but with a deamplification step causing a decrease in active length where an identically located amplification step would cause an increase in active length and with a deamplification step causing an increase in active length where an identically located amplification step would cause a decrease in active length. Being able to lengthen or shorten the active length of an ultrasonic surgical blade offers advantages for particular surgical applications, as can be appreciated by those skilled in the art.

The foregoing description of several expressions and embodiments of the invention has been presented for purposes of illustration. It is not intended to be exhaustive or to limit the invention to the precise forms disclosed, and obviously many modifications and variations are possible in light of the above teaching. For example, as would be apparent to those skilled in the art, the disclosures herein of the ultrasonic surgical blade and ultrasonic surgical instrument have equal application in robotic assisted surgery taking into account the obvious modifications of such systems, components and methods to be compatible with such a robotic system.

What is claimed is:

1. An ultrasonic surgical blade comprising an ultrasonic-surgical-blade body having a distal tip which is a most-distal vibration antinode, having a most-distal vibration node, having a second-most-distal vibration antinode, and having a gain step, wherein the gain step is disposed between the second-most-distal vibration antinode and the distal tip, and wherein the gain step is spaced apart from the most-distal vibration node by a gain-step distance greater than 5% of the distance between the second-most-distal vibration antinode and the distal tip.

2. The ultrasonic surgical blade of claim 1, wherein the gain-step distance is bedtween substantially 25% and substantially 45% of the distance between the second-most-distal vibration antinode and the distal tip.

3. The ultrasonic surgical blade of claim 1, wherein, between the second-most-distal vibration antinode and the distal tip, the maximum vibration amplitude of the ultrasonic-surgical-blade body proximal the gain step is less than the maximum vibration amplitude of the ultrasonic-surgical-blade body distal the gain step.

4. The ultrasonic surgical blade of claim 1, wherein, between the second-most-distal vibration antinode and the distal tip, the maximum vibration amplitude of the ultrasonic-surgical-blade body proximal the gain step is greater than the maximum vibration amplitude of the ultrasonic-surgical-blade body distal the gain step.

5. The ultrasonic surgical blade of claim 1, wherein the gain step is disposed between the most-distal vibration node and the distal tip.

6. The ultrasonic surgical blade of claim 1, wherein the gain step is disposed between the most-distal vibration node and the second-most-distal vibration antinode.

7. The ultrasonic surgical blade of claim 1, wherein the ultrasonic-surgical-blade body has a longitudinal axis and consists essentially of a first geometric solid having a substantially constant first transverse cross-sectional area from the gain step to the distal tip and a second geometric solid having a substantially constant second transverse cross-sectional area from the gain step to the second-mostdistal vibration antinode, wherein the second transverse cross-sectional area is different than the first transverse cross-sectional area.

8. The ultrasonic surgical blade of claim 7, wherein the shape and size of the first external perimeter of the first transverse cross-sectional area is substantially equal to the shape and size of the second external perimeter of the second transverse cross-sectional area.

9. The ultrasonic surgical blade of claim 1, wherein the ultrasonic-surgical-blade body has a longitudinal axis and is substantially symmetrical about the longitudinal axis.

10. The ultrasonic surgical blade of claim 1, wherein the ultrasonic-surgical-blade body has an additional gain step which is spaced-apart from the gain step, which is disposed between the second-most-distal vibration antinode and the distal tip, and which is spaced apart from the most-distal vibration node by a gain-step distance greater than 5% of the distance between the second-most-distal vibration antinode and the distal tip, wherein the ultrasonic-surgical-blade body has a longitudinal axis and a longitudinally hole, and wherein the longitudinal hole has a shoulder defining the additional gain step.

11. An ultrasonic surgical instrument comprising:
 a) a handpiece including an ultrasonic transducer;
 b) an ultrasonic transmission rod having a proximal end and a distal end, wherein the proximal end is operatively connected to the ultrasonic transducer; and
 c) an ultrasonic surgical blade activated by the distal end and including an ultrasonic-surgical-blade body having a distal tip which is a most-distal vibration antinode, having a most-distal vibration node, having a second-most-distal vibration antinode, and having a gain step, wherein the gain step is disposed between the second-most-distal vibration antinode and the distal tip, and wherein the gain step is spaced apart from the most-distal vibration node by a gain-step distance greater than 5% of the distance between the second-most-distal vibration antinode and the distal tip.

12. An ultrasonic surgical blade comprising an ultrasonic-surgical-blade body having, in any half wave length of the ultrasonic-surgical-blade body, a first vibration antinode, a vibration node, a second vibration antinode, and a gain step, wherein the gain step is disposed between the second vibration antinode and the first vibration antinode, and wherein the gain step is spaced apart from the vibration node by a gain-step distance greater than 5% of the distance between the second vibration anti node and the first vibration antinode.

* * * * *